(12) United States Patent
Collings et al.

(10) Patent No.: US 10,251,661 B2
(45) Date of Patent: *Apr. 9, 2019

(54) HAND HELD ELECTROMECHANICAL SURGICAL HANDLE ASSEMBLY FOR USE WITH SURGICAL END EFFECTORS, AND METHODS OF USE

(71) Applicant: Covidien LP, Mansfield, MA (US)

(72) Inventors: Peter T. Collings, Shelton, CT (US); Xingrui Chen, Glastonbury, CT (US); Luis Dussan, East Haven, CT (US); Kelly Valentine, Newington, CT (US)

(73) Assignee: Covidien LP, Mansfield, MA (US)

( * ) Notice: Subject to any disclaimer, the term of this patent is extended or adjusted under 35 U.S.C. 154(b) by 133 days.

This patent is subject to a terminal disclaimer.

(21) Appl. No.: 15/364,733

(22) Filed: Nov. 30, 2016

(65) Prior Publication Data

US 2017/0079674 A1  Mar. 23, 2017

Related U.S. Application Data (63) Continuation of application No. 14/247,312, filed on Apr. 8, 2014, now Pat. No. 9,539,006.

(Continued)

(51) Int. Cl.
*A61B 17/072* (2006.01)
*A61B 17/29* (2006.01)
(Continued)

(52) U.S. Cl.
CPC .... *A61B 17/2909* (2013.01); *A61B 17/00234* (2013.01); *A61B 17/068* (2013.01);
(Continued)

(58) Field of Classification Search
CPC .............. A61B 17/068; A61B 17/072; A61B 17/07207; A61B 17/00234; A61B 17/115;
(Continued)

(56) References Cited

U.S. PATENT DOCUMENTS

| | | | |
|---|---|---|---|
| 4,091,880 A | 5/1978 | Troutner et al. | |
| 4,522,270 A | 6/1985 | Kishi | |

(Continued)

FOREIGN PATENT DOCUMENTS

| | | |
|---|---|---|
| EP | 2283780 A2 | 2/2011 |
| EP | 2491867 A1 | 8/2012 |

(Continued)

OTHER PUBLICATIONS

Extended European Search Report corresponding to EP 14 18 2234.6, completed Feb. 20, 2015 and dated Mar. 3, 2015; (4 pp).

(Continued)

*Primary Examiner* — Scott A Smith (57) ABSTRACT

The present disclosure relates to hand held electromechanical powered surgical handle assemblies for use with surgical end effectors capable of clamping, cutting and/or stapling tissue and methods of use thereof. The surgical device includes a handle assembly and a drive unit assembly removably and selectively connectable to a selected first connecting feature and second connecting feature of the handle assembly. The drive unit assembly includes a motor and a drive shaft driven by the motor.

19 Claims, 6 Drawing Sheets

Related U.S. Application Data (60) Provisional application No. 61/870,324, filed on Aug. 27, 2013.

(51) Int. Cl.

| | | |
|---|---|---|
| *A61B 17/00* | (2006.01) | |
| *A61B 17/068* | (2006.01) | |
| *A61B 17/285* | (2006.01) | |
| *A61B 17/32* | (2006.01) | |
| *A61B 17/295* | (2006.01) | |
| *G05G 11/00* | (2006.01) | |
| *A61B 17/115* | (2006.01) | |

(52) U.S. Cl.
CPC ...... *A61B 17/072* (2013.01); *A61B 17/07207* (2013.01); *A61B 17/285* (2013.01); *A61B 17/295* (2013.01); *A61B 17/320016* (2013.01); *G05G 11/00* (2013.01); *A61B 17/115* (2013.01); *A61B 2017/0003* (2013.01); *A61B 2017/0042* (2013.01); *A61B 2017/0046* (2013.01); *A61B 2017/00221* (2013.01); *A61B 2017/00389* (2013.01); *A61B 2017/00398* (2013.01); *A61B 2017/00464* (2013.01); *A61B 2017/00477* (2013.01); *A61B 2017/00734* (2013.01); *A61B 2017/07285* (2013.01); *A61B 2017/291* (2013.01); *A61B 2017/2912* (2013.01); *A61B 2017/2925* (2013.01); *Y10T 29/49002* (2015.01)

(58) Field of Classification Search
CPC .......... A61B 17/1155; A61B 17/07278; A61B 2017/00398; A61B 2017/00473; A61B 2017/00039; A61B 2017/07214
USPC .. 227/19, 175.1, 175.2, 176.1, 178.1, 180.1; 606/139, 143, 151, 153, 205, 219
See application file for complete search history.

(56) References Cited

U.S. PATENT DOCUMENTS

| | | |
|---|---|---|
| 4,759,240 A | 7/1988 | Lin |
| 4,962,681 A | 10/1990 | Yang |
| 5,149,230 A | 9/1992 | Nett |
| 5,372,420 A | 12/1994 | Van Deursen et al. |
| 5,553,675 A | 9/1996 | Pitzen et al. |
| 5,575,799 A | 11/1996 | Bolanos et al. |
| 5,653,374 A | 8/1997 | Young et al. |
| 5,779,130 A | 7/1998 | Alesi et al. |
| 5,849,023 A | 12/1998 | Mericle |
| 5,863,159 A | 1/1999 | Lasko |
| 6,013,126 A | 1/2000 | Shannon et al. |
| 6,102,134 A | 8/2000 | Alsruhe |
| D443,491 S | 6/2001 | Robson |
| D447,924 S | 9/2001 | Neitzell et al. |
| 6,321,856 B1 | 11/2001 | Alsruhe |
| 6,364,033 B1 | 4/2002 | Hung et al. |
| 6,506,002 B1 | 1/2003 | Cummins |
| 6,517,565 B1 | 2/2003 | Whitman et al. |
| 6,715,969 B2 | 4/2004 | Eriksen |
| 6,716,233 B1 | 4/2004 | Whitman |
| 6,887,244 B1 | 5/2005 | Walker et al. |
| 7,055,622 B2 | 6/2006 | Bone |
| 7,066,692 B2 | 6/2006 | Kuhn |
| 7,371,033 B2 | 5/2008 | Whitehead |
| 7,673,783 B2 | 3/2010 | Morgan et al. |
| 7,823,760 B2 | 11/2010 | Zemlok et al. |
| 7,887,530 B2 | 2/2011 | Zemlok et al. |
| 7,918,230 B2 | 4/2011 | Whitman et al. |
| 7,922,063 B2 | 4/2011 | Zemlok et al. |
| 7,931,660 B2 | 4/2011 | Aranyi et al. |
| 7,963,433 B2 | 6/2011 | Whitman et al. |
| 7,997,835 B2 | 8/2011 | Whitehead et al. |
| 8,016,855 B2 | 9/2011 | Whitman et al. |
| 8,267,924 B2 | 9/2012 | Zemlok et al. |
| 8,479,969 B2 | 7/2013 | Shelton, IV |
| 8,795,324 B2 | 8/2014 | Kawai et al. |
| 9,539,006 B2 | 1/2017 | Collings et al. |
| 2004/0092912 A1 | 5/2004 | Jinno et al. |
| 2005/0187576 A1 | 8/2005 | Whitman et al. |
| 2006/0190027 A1* | 8/2006 | Downey ................ A61B 17/29 606/205 |
| 2008/0185419 A1 | 8/2008 | Smith et al. |
| 2009/0031842 A1 | 2/2009 | Kawai et al. |
| 2009/0314821 A1 | 12/2009 | Racenet |
| 2010/0016855 A1 | 1/2010 | Ramstein et al. |
| 2010/0331859 A1* | 12/2010 | Omori ................ A61B 17/4241 606/130 |
| 2011/0125138 A1 | 5/2011 | Malinouskas et al. |
| 2013/0324978 A1 | 12/2013 | Nicholas et al. |
| 2014/0012237 A1 | 1/2014 | Pribanic et al. |

FOREIGN PATENT DOCUMENTS

| | | |
|---|---|---|
| EP | 2505147 A1 | 10/2012 |
| JP | 2011004880 A | 1/2011 |
| WO | 2004091377 A2 | 10/2004 |

OTHER PUBLICATIONS

Extended European Search Report dated Oct. 13, 2017 in corresponding European Patent Application No. 17178528.0, 9 pages.

\* cited by examiner

HAND HELD ELECTROMECHANICAL SURGICAL HANDLE ASSEMBLY FOR USE WITH SURGICAL END EFFECTORS, AND METHODS OF USE

CROSS-REFERENCE TO RELATED APPLICATIONS

This application is a continuation of U.S. patent application Ser. No. 14/247,312 filed Apr. 8, 2014, which claims the benefit of and priority to U.S. Provisional Patent Application No. 61/870,324, filed Aug. 27, 2013, the entire disclosure of which is incorporated by reference herein.

BACKGROUND

1. Technical Field

The present disclosure relates to surgical devices and/or systems and their methods of use. More specifically, the present disclosure relates to hand held electromechanical powered surgical handle assemblies for use with surgical end effectors capable of clamping, cutting and/or stapling tissue and methods of use thereof.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a handle assembly, which is reusable, and a disposable end effector or the like that is selectively connected to the handle assembly prior to use and then disconnected from the end effector following use in order to be disposed of or in some instances sterilized for re-use.

The handle assemblies come in a variety of configurations and/or orientations, typically in a pistol-grip configuration or an in-line configuration. A surgeon will select the configuration of the handle assembly based on comfort of use or needs that exist to perform the surgical procedure. If needed, a surgeon may have both a pistol-grip handle assembly and an in-line handle assembly available and may interchange the handle assemblies during the surgical procedure as needed or desired.

In view of the foregoing, it would be highly advantageous to provide a surgical system including a handle assembly that is capable of changing a configuration of the surgical system between at least a pistol-grip configuration or an in-line configuration, wherein the handle assembly is adaptable to accommodate different methods of holding and handling the surgical system during operation.

SUMMARY

The present disclosure relates to hand held electromechanical powered surgical handle assemblies for use with surgical end effectors capable of clamping, cutting and/or stapling tissue and methods of use thereof.

According to an aspect of the present disclosure, a powered, hand held, electromechanical surgical device, includes a handle assembly including a handle housing defining a longitudinal axis, the handle housing including a first connecting feature and a second connecting feature; a circuit board disposed within the handle housing; a battery disposed within the handle housing and being in electrical communication with the circuit board; at least one electrical contact associated with the first connecting feature of the handle housing and being in electrical communication with the circuit board and battery; at least one electrical contact associated with the second connecting feature of the handle housing and being in electrical communication with the circuit board and battery; and at least one first button for actuation by a finger of a user, each firing button being in electrical communication with the circuit board.

The surgical device further includes a drive unit assembly removably and selectively connectable to a selected one of the first connecting feature and the second connecting feature of the handle assembly. The drive unit assembly includes a drive unit housing defining a longitudinal axis, the drive unit housing including a connecting feature configured and adapted to mate with a selected one of the first connecting feature and the second connecting feature of the handle assembly; a motor disposed within the drive unit housing; a drive shaft rotatably supported in and extending from the drive unit housing, the drive shaft being driven by the motor; and at least one electrical contact associated with the connecting feature of the drive unit housing and being in electrical communication with the motor.

According to an aspect of the present disclosure, when the drive unit assembly is connected to the first connecting feature of the handle assembly an electrical contact associated with the connecting feature of the drive unit housing electrically interfaces with an electrical contact of the first connecting feature of the handle housing; and the longitudinal axis of the drive unit assembly is parallel relative to the longitudinal axis of the handle housing.

Also according to an aspect of the present disclosure, when the drive unit assembly is connected to the second connecting feature of the handle assembly an electrical contact associated with the connecting feature of the drive unit housing electrically interfaces with an electrical contact of the second connecting feature of the handle housing; and the longitudinal axis of the drive unit assembly is angled relative to the longitudinal axis of the handle housing.

The handle assembly may include at least one second button for actuation by a thumb of the user.

The drive unit assembly may include a plurality of drive shafts rotatably supported in and extending from the drive unit housing, wherein each drive shaft is driven by the motor.

The first connecting feature may be located at a longitudinally distal-most surface of the handle housing. The second connecting feature may be located on a lateral side surface of the handle housing.

The handle assembly may include an attachment feature associated with each of the first connecting feature and the second connecting feature. The drive unit assembly may include an attachment feature configured for selective connection to a selected one of the attachment features of the handle assembly.

Each attachment feature of the handle assembly may include a recess formed in a surface of the handle assembly. The attachment feature of the drive unit assembly may include a latch assembly configured for selective receipt in a selected recess of the handle assembly.

The handle assembly and the drive unit assembly may be in wireless communication with one another.

According to another aspect of the present disclosure, a method of configuring a powered, hand held, electromechanical surgical device is provided. The method includes the step of providing a handle assembly. The handle assembly includes a handle housing defining a longitudinal axis, the handle housing including a first connecting feature and a second connecting feature; a circuit board disposed within the handle housing; a battery disposed within the handle housing and being in electrical communication with the circuit board; at least one electrical contact associated with the first connecting feature of the handle housing and being in electrical communication with the circuit board and battery; and at least one electrical contact associated with the second connecting feature of the handle housing and being in electrical communication with the circuit board and battery; at least one first button for actuation by a finger of a user, each firing button being in electrical communication with the circuit board.

The method further includes the step of providing a drive unit assembly removably and selectively connectable to a selected one of the first connecting feature and the second connecting feature of the handle assembly. The drive unit assembly includes a drive unit housing defining a longitudinal axis, the drive unit housing including a connecting feature configured and adapted to mate with a selected one of the first connecting feature and the second connecting feature of the handle assembly; a motor disposed within the drive unit housing; a drive shaft rotatably supported in and extending from the drive unit housing, the drive shaft being driven by the motor; and at least one electrical contact associated with the connecting feature of the drive unit housing and being in electrical communication with the motor.

The method further includes the steps of connecting the drive unit assembly to the first connecting feature of the handle assembly, wherein the longitudinal axis of the drive unit assembly is parallel relative to the longitudinal axis of the handle housing, when an in-line configuration of the surgical device is desired; and connecting the drive unit assembly to the second connecting feature of the handle assembly, wherein the longitudinal axis of the drive unit assembly is angled relative to the longitudinal axis of the handle housing, when a pistol-grip configuration of the surgical device is desired.

The method may further include the step of electrically interfacing an electrical contact associated with the connecting feature of the drive unit housing with an electrical contact of the first connecting feature of the handle housing when the drive unit assembly is connected to the first connecting feature of the handle assembly.

The method may further include the step of electrically interfacing an electrical contact associated with the connecting feature of the drive unit housing with an electrical contact of the second connecting feature of the handle housing when the drive unit assembly is connected to the second connecting feature of the handle assembly.

The method may further include the step of connecting an end effector to the drive shaft of the drive unit assembly.

The method may further include the steps of connecting an adapter to the drive shaft of the drive unit assembly; and connecting an end effector to the adapter. The adapter may transmit a rotative force from the drive shaft of the motor to the end effector.

The handle assembly and the drive unit assembly may be in wireless communication with one another.

BRIEF DESCRIPTION OF THE DRAWINGS

Embodiments of the present disclosure are described herein with reference to the accompanying drawings, wherein.

DETAILED DESCRIPTION OF EMBODIMENTS

Embodiments of the presently disclosed surgical systems and/or handle assemblies are described in detail with reference to the drawings, in which like reference numerals designate identical or corresponding elements in each of the several views. As used herein the term "distal" refers to that portion of the surgical system and/or handle assembly, or component thereof, farther from the user, while the term "proximal" refers to that portion of the surgical system and/or handle assembly, or component thereof, closer to the user.

A surgical device, in accordance with an embodiment of the present disclosure, is generally designated as 100, and is in the form of a powered hand held electromechanical handle assembly configured for selective attachment thereto of a plurality of different end effectors, either directly thereto or through an adapter, that are each configured for actuation and manipulation by the powered hand held electromechanical surgical handle assembly.

As illustrated in FIGS. 1 and 3-5, surgical device 100 includes a hand-grip or handle assembly 102 configured for gripping by a hand of a user or surgeon. Handle assembly 102 includes a housing 104 defining a longitudinal axis "X1," and a transverse axis "Y1."

Figures 1, 2:
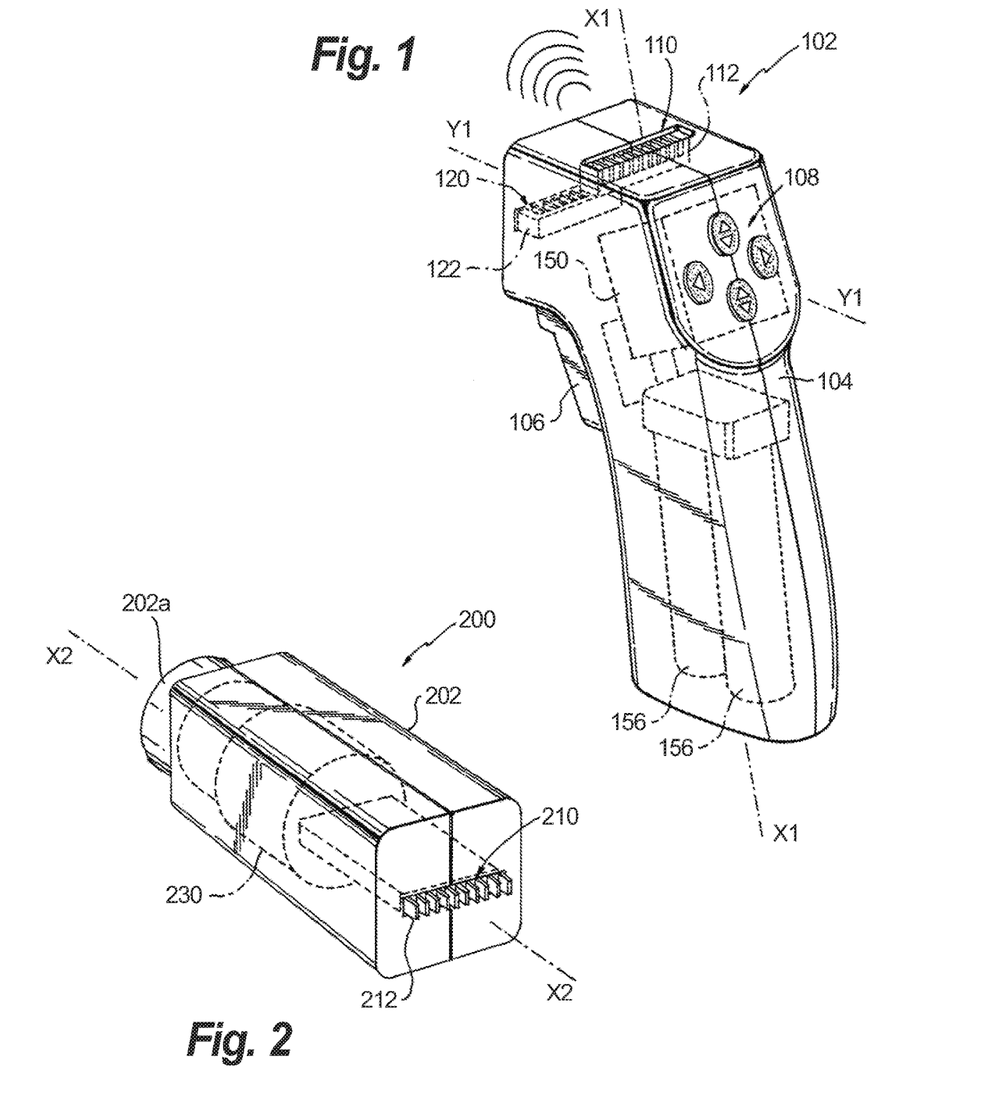
FIG. 1 is rear, perspective, schematic illustration of a handle assembly of a surgical device of the present disclosure.
FIG. 2 is rear, perspective, schematic illustration of a drive unit assembly of the surgical device of the present disclosure.

Housing 104 of handle assembly 102 houses a circuit board 150. Circuit board 150 is configured to control the various operations of surgical device 100.

Housing 104 of handle assembly 102 also removably or non-removably houses a battery 156 therein. Battery 156 may be rechargeable, non-rechargeable, re-useable and/or disposable. Battery 156 is configured to supply power to any of the electrical components of surgical device 100.

Housing 104 of handle assembly 102 supports at least one trigger or button 106 on a surface or side thereof for engagement by an index finger of the user or surgeon. Housing 104 of handle assembly 102 further supports at least one other trigger or button 108 on a surface or side thereof for engagement by a thumb of the user or surgeon.

It is contemplated that trigger and/or button 106, 108 may be in the form of trigger switches, Hall Effect switches, pressure switches, contact switches, touch pads, inductance switches, dials, toggles, rockers, wheels and the like.

The actuation of trigger 106 or 108 causes circuit board 150 to provide appropriate signals to a drive unit assembly 200 (as will be discussed in greater detail below) to close a tool assembly 304 of end effector 300 (see FIGS. 5 and 6) and/or to fire a stapling/cutting cartridge within tool assembly 304 of end effector 300, to open tool assembly 304, to articulate tool assembly 304 relative to body portion 302, and/or to rotate tool assembly 304 relative to handle housing 102.

As can be seen in FIGS. 1 and 3-5, housing 104 of handle assembly 102 includes a first connecting assembly or feature 110 formed or provided in/on a first surface or side thereof, and a second connecting assembly or feature 120 formed or provided in/on a second surface or side thereof. Each connecting feature 110, 120 includes a respective electrical contact or terminal 112, 122 associated therewith which is in electrical communication with circuit board 150 and battery 156.

With reference to FIGS. 2-5, surgical device 100 further includes a drive unit assembly 200 selectively connectable to either first connecting feature 110 or second connecting feature 120 of handle assembly 102. Specifically, drive unit assembly 200 includes a housing 202 defining a longitudinal axis "X2".

Housing 202 of drive unit assembly 200 includes a connecting feature 210 configured and adapted to selectively and removably connect with either first connecting feature 110 or second connecting feature 120 of handle assembly 102. Connecting feature 210 includes a respective electrical contact or terminal 212 associated therewith which is in electrical communication with a motor 230 (as will be discussed in greater detail below).

For example, in an embodiment, each connecting feature 110, 120 of handle assembly 102 may be in the form of a male plug for insertion into connecting feature 210 of drive unit assembly 200 which may be in the from of a female receptacle, or vice-versa. It is envisioned that the interface between connecting feature 210 of drive unit assembly 200 and either first connecting feature 110 or second connecting feature 120 of handle assembly 102 may be in the form of a snap-fit connection, bayonet-type connection or the like.

Figure 3:
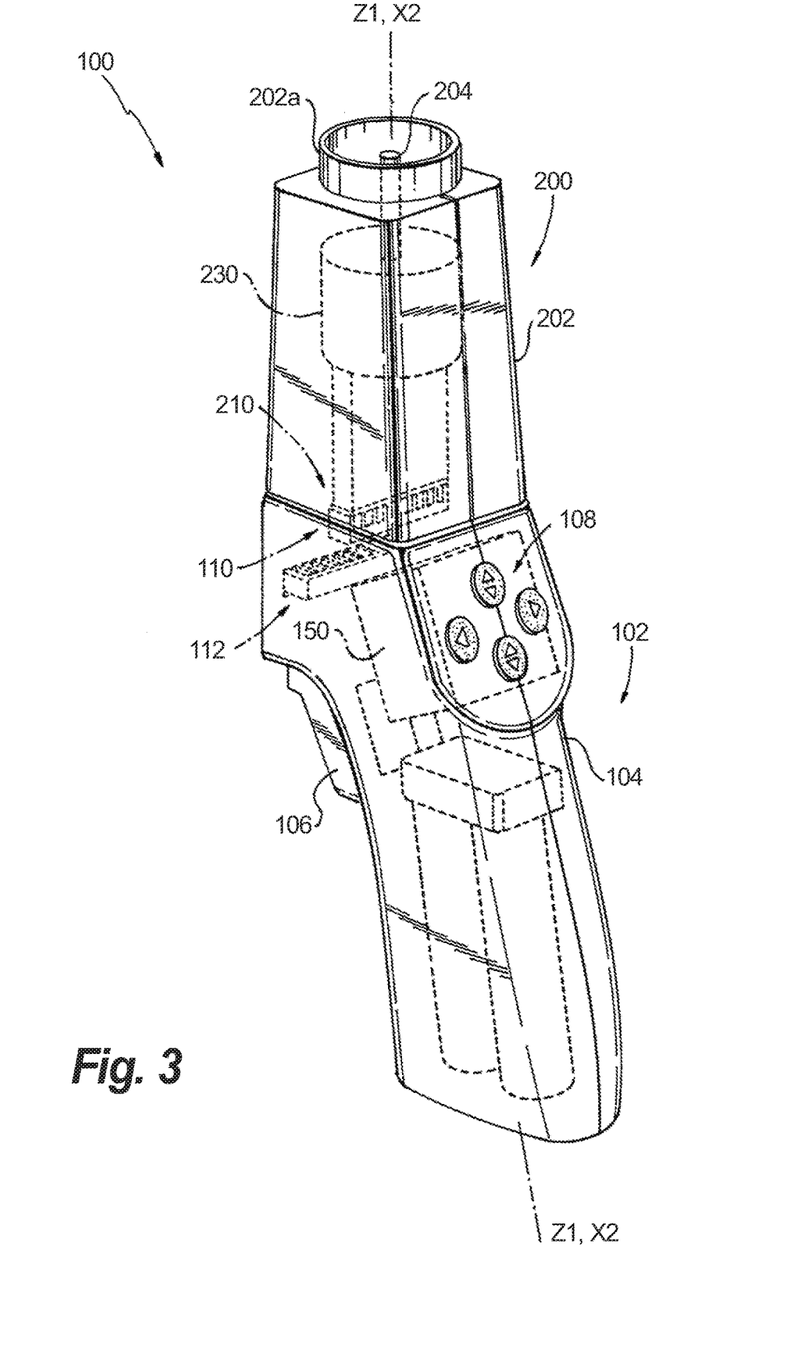
FIG. 3 is a perspective, schematic illustration of the surgical device of the present disclosure, shown in a first configuration.

As can be seen in FIG. 3, when drive unit assembly 200 is connected to first connecting feature 110 of handle assembly 102, longitudinal axis "X2" of drive unit assembly 200 is oriented substantially parallel or co-axial with longitudinal axis "X1" of handle housing 104 of handle assembly 102.

Figure 4:
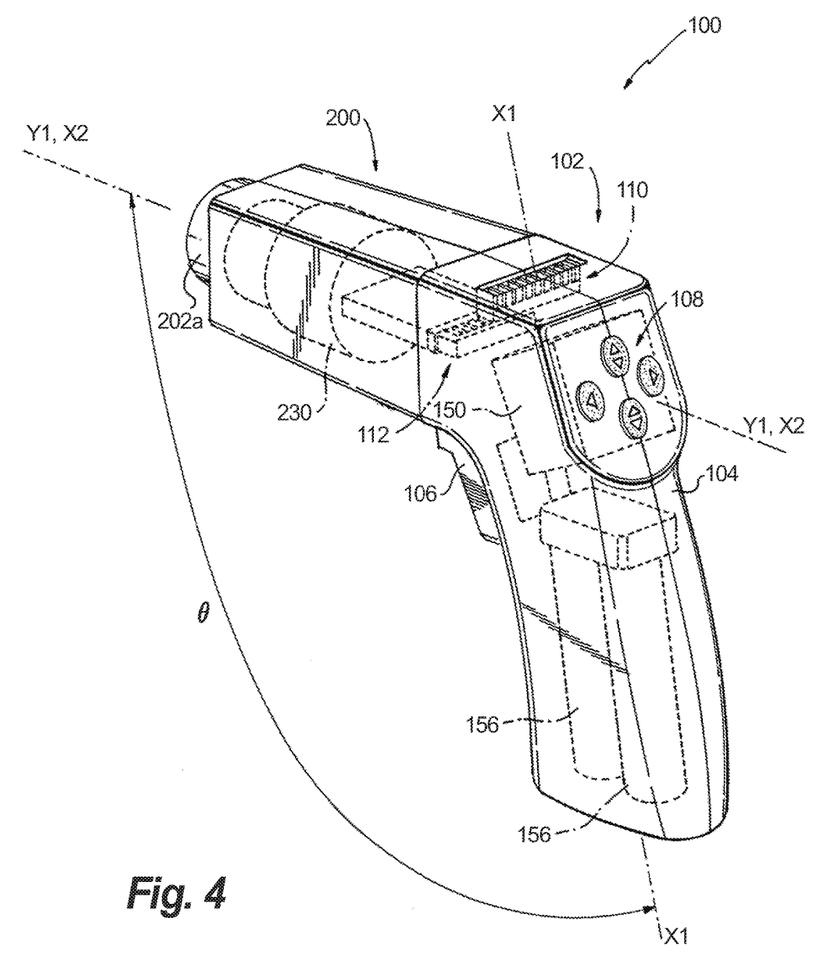
FIG. 4 is a perspective, schematic illustration of the surgical device of the present disclosure, shown in a second configuration.

Further, as can be seen in FIG. 4, when drive unit assembly 200 is connected to second connecting feature 120 of handle assembly 102, longitudinal axis "X2" of drive unit assembly 200 is oriented at an angle "θ", between about 45° and about 135°, relative to longitudinal axis "X1" of handle housing 104 of handle assembly 102. Alternatively, as can also be seen in FIG. 4, when drive unit assembly 200 is connected to second connecting feature 120 of handle assembly 102, longitudinal axis "X2" of drive unit assembly 200 may be oriented substantially parallel to or co-axial with transverse axis "Y1" of handle housing 104 of handle assembly 102.

Housing 202 of drive unit assembly 200 supports at least one motor 230 therein. Motor 230 may be brushed or brushless. Housing 202 may include heat dissipating features in the form of slits, apertures or the like formed therein, or in the form of heat sinks.

Drive unit housing 202 of drive unit assembly 200 supports at least one electrical contact or receptacle 212 for selective electrical connection to a respective electrical contact or terminal 112, 122 of connecting feature 110, 120 of handle assembly 102 when drive unit assembly 200 is connected to handle assembly 102. Electrical contact 212 is in electrical communication with motor 230. In this manner, when drive unit assembly 200 is connected to handle assembly 102, motor 230 is in electrical communication with circuit board 150 and battery 156 of handle assembly 102.

Figure 5:
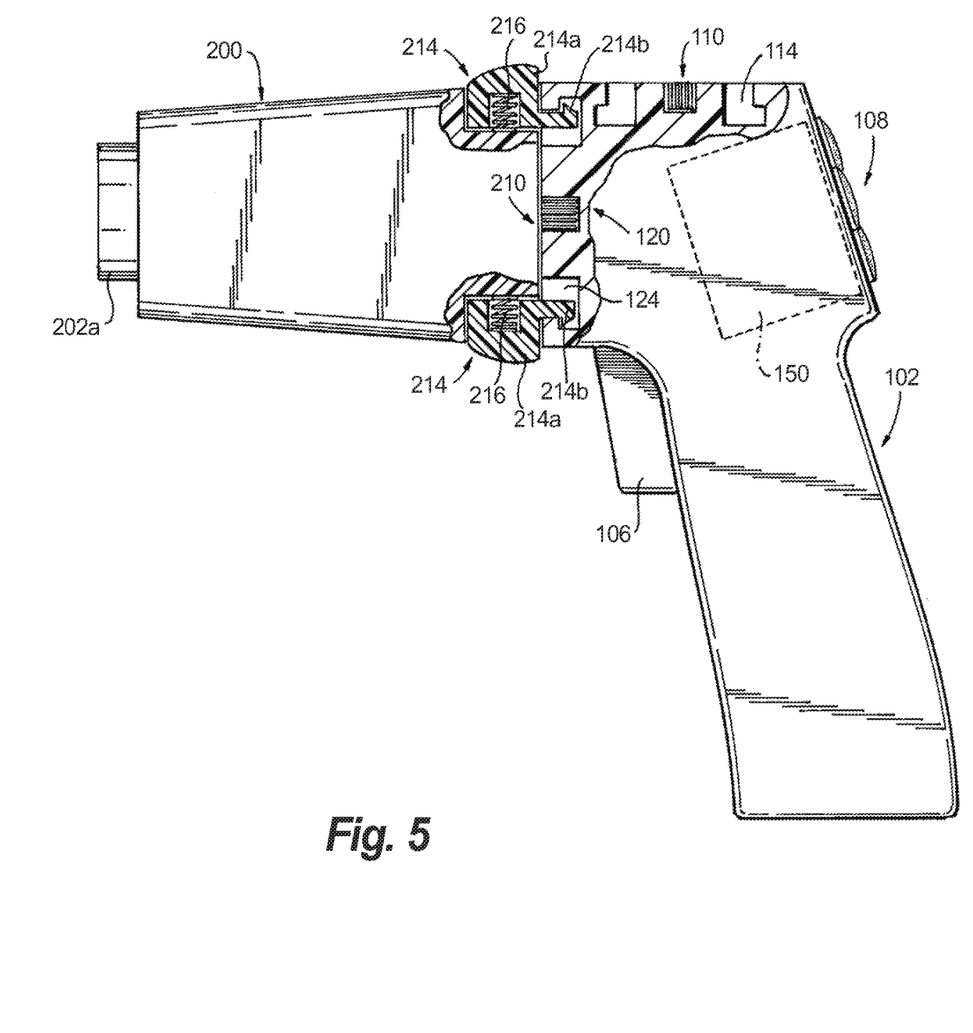
FIG. 5 is a side, elevational schematic view of the surgical device as illustrated in FIG. 4, with portions thereof shown in cross-section.

As illustrated in FIG. 5, handle assembly 102 and drive unit assembly 200 include complementary attachment features which permit selective connection/disconnection of handle assembly 102 and drive unit assembly 200 to/from one another. Specifically, handle assembly 102 may include a first attachment recess 114 associated with connecting feature 110 of handle assembly 102, and a second attachment recess 124 associated with connecting feature 120 of handle assembly 102. Additionally, the attachment feature of drive unit assembly 200 may include a latch assembly 214 associated with connecting feature 210. Latch assembly 214 may include at least one latch 214a that is biased to a radially outward position by a biasing member 216 or the like (i.e., spring). Each latch 214a may be moved radially inward, against the bias of the biasing member 216, so that fingers 214b of latches 214a enter into a selected one of first attachment recess 114 or second attachment recess 124 of handle assembly 102. Thereafter, each latch 214a may be released to complete the connection of handle assembly 102 and drive unit assembly 200. It is contemplated that latch assembly 214 may be configured as a snap-latch assembly wherein fingers 214b cams into respective recess 114, 124 simply upon approximation of drive unit assembly 200.

While a latch assembly 214 is shown supported on drive unit assembly 200, it is contemplated that multiple latch assemblies may be provided on handle assembly and that a complementary recess may be provided in drive unit assembly. Additionally, it is contemplated that selective connection/disconnection of handle assembly 102 and drive unit assembly 200 to/from one another may be accomplished using any number of features, including and not limited to a locking pin/rod/post arrangement, a retractable collar and ball pin arrangement and the like.

Figure 6:
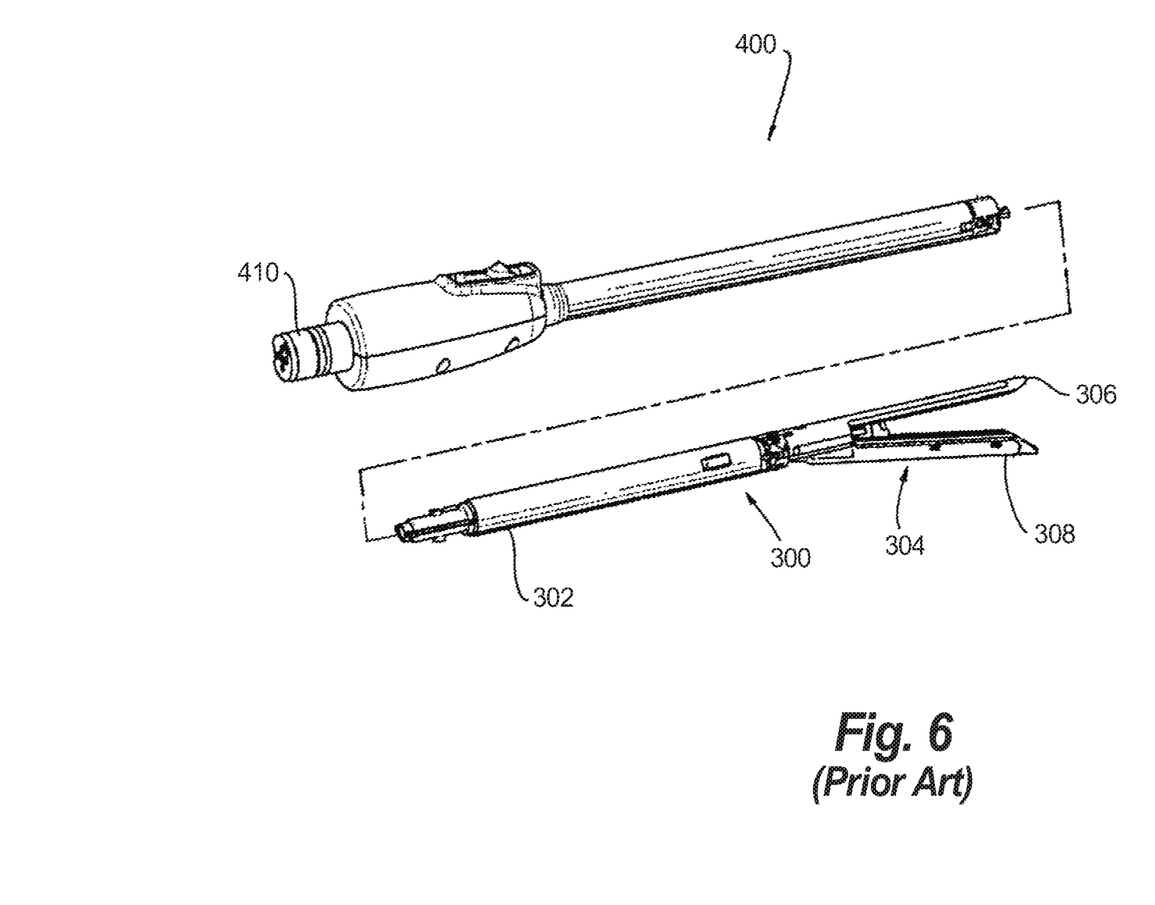
FIG. 6 is a perspective view of a prior art adapter assembly and an end effector for use with the surgical device of the present disclosure.
Figure 7:
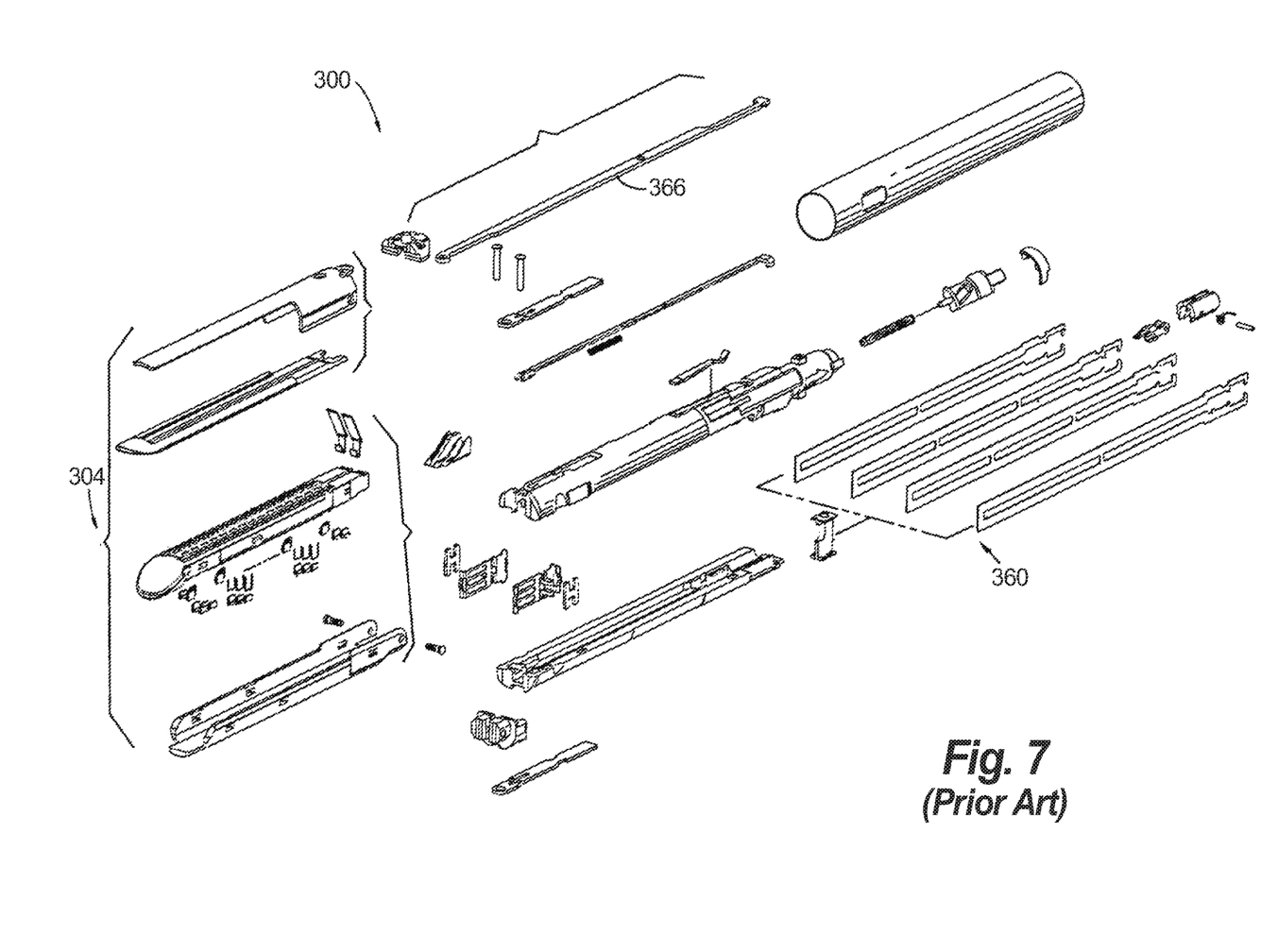
FIG. 7 is an exploded perspective view of the prior art end effector of FIG. 6.

As can be seen in FIGS. 2-5, drive unit housing 202 of drive unit assembly 200 defines a distal connecting portion 202a configured to accept a corresponding drive coupling assembly 410 of an adapter assembly 400 (see FIG. 6) or of an end effector 300 (see FIGS. 6 and 7). The specific construction and operation of an exemplary adapter assembly 400, for use with drive unit assembly 200 and surgical device 100 of the present disclosure, is shown and described in U.S. patent application Ser. No. 13/904,497, filed on May 29, 2013, (U.S. Patent Publication No. 2014-0012237 A1), or U.S. patent application Ser. No. 13/875,571, filed on May 2, 2013, (U.S. Patent Publication No. 2013-0324978 A1), the entire content of each of which is incorporated herein by reference. The adapter assembly 400 is configured to convert a rotative force of each rotatable drive shaft of drive unit assembly 200 into an axial translative force useful for operating a drive assembly 360 and/or an articulation link 366 of end effector 300, as illustrated in FIG. 7.

Connecting portion 202a of drive unit housing 202 may define a cylindrical recess that receives a drive coupling assembly 410 of adapter assembly 400 when adapter assembly 400 is mated to drive unit housing 202. Connecting portion 202a of drive unit housing 202 rotatably supports at least one rotatable drive shaft 204 (see FIG. 3) extending from or being driven by motor 230.

When adapter assembly 400 is mated to connecting portion 202a of drive unit housing 202, each of rotatable drive shafts 204 of connecting portion 202a of drive unit housing 202 couples with a corresponding rotatable connector sleeve (not shown) of adapter assembly 400. Specifically, for example, the interface between a corresponding drive shaft 204 and a connector sleeve are keyed such that rotation of drive shaft 204 of connecting portion 202a of drive unit housing 202 causes a corresponding rotation of the corresponding connector sleeve of adapter assembly 400.

The mating of each of drive shafts 204 of connecting portion 202a of drive unit housing 202 with corresponding connector sleeves of adapter assembly 400 allows rotational forces to be independently transmitted via each of the respective connector interfaces. Drive shafts 204 of connecting portion 202a of drive unit housing 202 may be configured to be independently rotated by motor 230. If multiple drive shafts are provided, drive unit assembly 200 may include a function selection module (not shown) which functions to select which drive shaft of the drive shafts 204 of connecting portion 202a of drive unit housing 202 is to be driven by motor 230.

Each of drive shafts 204 of connecting portion 202a of drive unit housing 202 has a keyed and/or substantially non-rotatable interface with respective connector sleeves of the adapter, wherein when the adapter is coupled to drive unit assembly 200, rotational force(s) are selectively transferred from motor 230 of drive unit assembly 200 to the adapter.

The selective rotation of drive shafts 204 of connecting portion 202a of drive unit housing 202 allows surgical device 100 to selectively actuate different functions of the end effector. As will be described in greater detail below, selective and independent rotation of a first drive shaft of drive shafts 204 of connecting portion 202a of drive unit housing 202 may correspond to the selective and independent opening and closing of a tool assembly of the end effector, and driving of a stapling/cutting component of the tool assembly of the end effector.

Also, the selective and independent rotation of a second drive shaft (not shown) of drive shafts 204 of connecting portion 202a of drive unit housing 202 may correspond to the selective and independent articulation of a tool assembly 304 of end effector 300 transverse to longitudinal axis "X2" of drive unit assembly 200 (see FIGS. 2-5). Additionally, the selective and independent rotation of a third drive shaft (not shown) of drive shafts 204 of connecting portion 202a of drive unit housing 202 may correspond to the selective and independent rotation of the end effector 300 about longitudinal axis "X2" of drive unit assembly 200.

In use, depending on the particular surgical procedure, depending on the particular end effectors to be utilized for the surgical procedure, and depending on the desired hand grip the surgeon prefers, desires or needs in order to perform the surgical procedure, the surgeon (or other operating room technician) selectively connects drive unit assembly 200 to either first connecting assembly or feature 110 formed or provided in/on the first surface or side of handle assembly 102 or second connecting assembly or feature 120 formed or provided in/on the second surface or side of handle assembly 102.

When drive unit assembly 200 is connected to first connecting assembly or feature 110 formed or provided in/on the first surface or side of handle assembly 102, the surgeon may grip surgical device 100 in an in-line of handshake grip fashion. When drive unit assembly 200 is connected to second connecting assembly or feature 120 formed or provided in/on the second surface or side of handle assembly 102, the surgeon may grip surgical device 100 in a pistol-grip fashion.

As illustrated in FIGS. 6 and 7, the end effector is designated as 300. End effector 300 is configured and dimensioned for endoscopic insertion through a cannula, trocar or the like. In particular, end effector 300 may pass through a cannula or trocar when end effector 300 is in a closed condition.

End effector 300 includes a proximal body portion 302 and a tool assembly 304. Proximal body portion 302 is releasably attached to a distal coupling of the adapter and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Proximal body portion 302 includes at least a drive assembly 360 and an articulation link 366.

Reference may be made to U.S. Patent Publication No. 2009/0314821, filed on Aug. 31, 2009, entitled "TOOL ASSEMBLY FOR A SURGICAL STAPLING DEVICE," the entire content of which is incorporated herein by reference, or U.S. patent application Ser. No. 13/904,497, filed on May 29, 2013, (U.S. Patent Publication No. 2014-0012237 A1), the entire content of which was previously incorporated herein by reference, for a detailed discussion of the construction and operation of end effector 300.

In an embodiment, it is contemplated that handle assembly 102 and drive unit assembly 200 may be provided with wireless communication components such that circuit board 150 of handle assembly 102 may wirelessly communicate with motor 230 of drive unit assembly 200. Examples of wireless communication components include, and are not limited to, Bluetooth, WIFI 802.11, zigby, etc.

In accordance with the present disclosure, information that may be communicated between handle assembly 102 and drive unit assembly 200 includes, and is not limited to information about motor control (i.e., current, speed, turns, torque), about forces, about switch activation, about system status (i.e., error/fault); information about an identification of components, about log information/usage counters; information about the environment (i.e., temperature, pressure, humidity); information about tissue properties (i.e., levels of oxygen, blood flow, tissue thickness); video/imaging information; and/or information about battery life/power.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A powered, hand held, electromechanical surgical device, comprising:
   a handle assembly including:
      a handle housing defining a longitudinal axis, the handle housing including a first connecting feature and a second connecting feature;
      a circuit board disposed within the handle housing;
      at least one electrical contact associated with the first connecting feature of the handle housing and being in electrical communication with the circuit board;
      at least one electrical contact associated with the second connecting feature of the handle housing and being in electrical communication with the circuit board; and
      at least one first firing button for actuation by a finger of a user, each first firing button being in electrical communication with the circuit board; and
   a drive unit assembly removably and selectively connectable to a selected one of the first connecting feature or the second connecting feature of the handle assembly, the drive unit assembly including:
      a drive unit housing defining a longitudinal axis, the drive unit housing including a connecting feature configured and adapted to mate with a selected one of the first connecting feature or the second connecting feature of the handle assembly;
      a motor disposed within the drive unit housing;
      a drive shaft rotatably supported in and extending from the drive unit housing, the drive shaft being driven by the motor; and
      at least on electrical contact associated with the connecting feature of the drive unit housing and being in electrical communication with the motor;
   wherein, when the drive unit assembly is connected to the first connecting feature of the handle assembly:
      an electrical contact associated with the connecting feature of the drive unit housing electrically interfaces with an electrical contact of the first connecting feature of the handle housing; and
      the longitudinal axis of the drive unit assembly is parallel relative to the longitudinal axis of the handle housing; and
   wherein, when the drive unit assembly is connected to the second connecting feature of the handle assembly:
      an electrical contact associated with the connecting feature of the drive unit housing electrically interfaces with an electrical contact of the second connecting feature of the handle housing; and
      the longitudinal axis of the drive unit assembly is angled relative to the longitudinal axis of the handle housing.

2. The surgical device according to claim 1, wherein the handle assembly includes at least one second button for actuation by a thumb of the user.

3. The surgical device according to claim 1, wherein the drive unit assembly includes a plurality of drive shafts rotatably supported in and extending from the drive unit housing, wherein each drive shaft is driven by the motor.

4. The surgical device according to claim 1, wherein the first connecting feature is located at a longitudinally distal-most surface of the handle housing.

5. The surgical device according to claim 4, wherein the second connecting feature is located on a lateral side surface of the handle housing.

6. The surgical device according to claim 1, wherein the handle assembly includes an attachment feature associated with each of the first connecting feature and the second connecting feature, and the drive unit assembly includes an attachment feature configured for selective connection to a selected one of the attachment features of the handle assembly.

7. The surgical device according to claim 6, wherein each attachment feature of the handle assembly comprises a recess formed in a surface of the handle assembly.

8. The surgical device according to claim 7, wherein the attachment feature of the drive unit assembly includes a latch assembly configured for selective receipt in a selected recess of the handle assembly.

9. The surgical device according to claim 1, wherein the handle assembly and the drive unit assembly are in wireless communication with one another.

10. The surgical device according to claim 1, wherein the handle assembly includes a battery disposed within the handle housing and being in electrical communication with the circuit board thereof.

11. The surgical device according to claim 10, wherein the at least one electrical contact associated with the first connecting feature of the handle housing is in electrical communication with the circuit board and the battery.

12. The surgical device according to claim 10, wherein the at least one electrical contact associated with the second connecting feature of the handle housing is in electrical communication with the circuit board and the battery.

13. The surgical device according to claim 10, wherein the at least one first firing button of the handle assembly is in electrical communication with the circuit board and battery.

14. A powered, hand held, electromechanical surgical device, comprising:
   a handle assembly including:
      a handle housing defining a longitudinal axis, the handle housing including a first connecting feature and a second connecting feature, wherein each connecting feature is configured to releasably engage a removable surgical drive unit assembly;
      a circuit board disposed within the handle housing;
      at least one electrical contact associated with the first connecting feature of the handle housing and being in electrical communication with the circuit board;
      at least one electrical contact associated with the second connecting feature of the handle housing and being in electrical communication with the circuit board; and
      at least one first firing button for actuation by a finger of a user, each first firing button being in electrical communication with the circuit board and a battery,
   wherein, the removable surgical drive unit assembly extends from the handle assembly in a first direction when releasably engaged to the first connecting feature, and the removable surgical drive unit assembly extends from the handle assembly in a second direction different from the first direction when releasably engaged to the second connecting feature.

15. The surgical device according to claim 14, further comprising a battery disposed within the handle housing and being in electrical communication with the circuit board, wherein the battery powers a motor of the removable surgical drive unit assembly when the removable surgical drive unit assembly is connected to the first connecting feature or the second connecting feature.

16. The surgical device according to claim 15, wherein the at least one electrical contact associated with the first connecting feature of the handle housing is in electrical communication with the circuit board and the battery.

17. The surgical device according to claim 16, wherein the at least one electrical contact associated with the second connecting feature of the handle housing is in electrical communication with the circuit board and the battery.

18. The surgical device according to claim 17, wherein each first firing button is in electrical communication with the circuit board and the battery.

19. A method of configuring a powered, hand held, electromechanical surgical device, the method comprising the steps of:
   releasably coupling a handle assembly to a drive unit assembly, the handle assembly including:
      a handle housing defining a longitudinal axis, the handle housing including a first connecting feature and a second connecting feature;
      a circuit board disposed within the handle housing;
      a battery disposed within the handle housing and being in electrical communication with the circuit board;
      at least one electrical contact associated with the first connecting feature of the handle housing and being in electrical communication with the circuit board and battery;
      at least one electrical contact associated with the second connecting feature of the handle housing and being in electrical communication with the circuit board and battery; and
      at least one first firing button for actuation by a finger of a user, each first firing button being in electrical communication with the circuit board; and
   the drive unit assembly configured to be removably and selectively connected to a selected one of the first connecting feature and the second connecting feature of the handle assembly, the drive unit assembly including:
      a drive unit housing defining a longitudinal axis, the drive unit housing including a connecting feature configured and adapted to mate with a selected one of the first connecting feature and the second connecting feature of the handle assembly;
      a motor disposed within the drive unit housing;
      a drive shaft rotatably supported in and extending from the drive unit housing, the drive shaft being driven by the motor; and
      at least one electrical contact associated with the connecting feature of the drive unit housing and being in electrical communication with the motor;
      wherein the drive unit assembly, extends from the handle housing in a first direction when removably and selectively connected to the first connecting feature of the handle assembly, the drive unit assembly and extends from the handle assembly in a second direction different from the first direction when removably and selectively connected to the second connecting feature.

* * * * *